United States Patent [19]
Hayafuji

[11] Patent Number: 5,964,704
[45] Date of Patent: Oct. 12, 1999

[54] INTRAOCULAR PRESSURE MEASURING APPARATUS

[75] Inventor: Mineki Hayafuji, Tokyo, Japan

[73] Assignee: Kabushiki Kaisha, Topcon, Tokyo, Japan

[21] Appl. No.: 09/108,736

[22] Filed: Jul. 1, 1998

[30] Foreign Application Priority Data

Jul. 4, 1997 [JP] Japan ................................. 9-179554

[51] Int. Cl.⁶ ....................................................... A61B 3/16
[52] U.S. Cl. .......................... 600/401; 600/558; 600/560
[58] Field of Search ................................... 600/401, 402, 600/403, 404, 405, 558, 559, 560

[56] References Cited

U.S. PATENT DOCUMENTS

| | | | |
|---|---|---|---|
| 4,832,039 | 5/1989 | Perry et al. | 600/493 |
| 4,860,760 | 8/1989 | Miyawaki et al. | 600/493 |
| 4,996,990 | 3/1991 | Hideshima | 600/401 |

*Primary Examiner*—Cary O'Connor
*Assistant Examiner*—Pamela L Wingood
*Attorney, Agent, or Firm*—Oppedahl & Larson LLP

[57] ABSTRACT

In the non-contact intraocular pressure measuring apparatus for measuring the intraocular pressure of the eye to be examined for a suitable measurement time, after alignment of the apparatus main body with the eye to be examined is performed, the time required for charging the condenser is calculated based on current supply time for the rotary solenoid at the time of the previous intraocular pressure measurement. When the calculated charging time elapses, the desired quantity of current is supplied from the condenser to the rotary solenoid, allowing the air supply unit to spray air to the cornea of the eye to be examined. The cornea is transfigured and flattened by the sprayed air. At the same time, intraocular pressure measuring light is illuminated from the intraocular pressure measuring optical system to the flattened cornea. The reflected light therefrom is detected to calculate intraocular pressure value of the eye to be examined.

6 Claims, 5 Drawing Sheets

INTRAOCULAR PRESSURE MEASURING APPARATUS

BACKGROUND OF THE INVENTION

1. Field of the invention

The present invention relates to a non-contact type intraocular pressure measuring apparatus for measuring intraocular pressure of the eye to be examined after the apparatus main body is aligned with the eye to be examined.

2. Description of Related Art

In the conventional non-contact type intraocular pressure measuring apparatus, an alignment light is projected on the cornea of the eye to be examined, and then the reflected alignment light is received to align the optical axis of the apparatus optical system with that of the eyeball. After the apparatus main body is aligned with the eye to be examined to secure a desired working distance, air is sprayed toward the cornea from a spraying nozzle provided that the spraying direction corresponds to the optical axis of the apparatus optical system to transfigure the cornea of the eye to be examined. Concurrently with the air spraying, an intraocular pressure measuring light is irradiated to the cornea and then the reflected light from the transfigured cornea is received, thus enabling non-contact measurement of intraocular pressure of the eye to be examined. The working distance represents a distance between the top of the cornea of the eye to be examined and the tip of the spraying nozzle.

In the above conventional type non-contact intraocular pressure measuring apparatus, a spraying nozzle is provided on the tip of an air supply unit having a cylinder with a piston, the piston is activated by a driving unit having solenoid. The solenoid is connected to a condenser which a charging circuit is connected to, and operated by current supplied from the condenser. The solenoid, thus operated by current supplied from the condenser that completes charging, activates a piston to cause a spraying nozzle to spray a fluid such as air to the cornea of the eye to be examined.

In the conventional intraocular pressure measuring apparatus, however, the completion of charging of the condenser for current supply to solenoid is determined by the elapse of the predetermined long charging time (for instance, three seconds). This is because if the condenser is always to be charged at a constant charging time, a long charging time must be set, considering that there is a wide variation in discharging quantity of the condenser between low intraocular pressure measurement where a small quantity of air is sprayed to the cornea and high intraocular pressure measurement where a large quantity of air is sprayed to the cornea. Thus it takes long time to measure intraocular pressure, causing a big burden to an examinee.

SUMMARY OF THE INVENTION

It is an object of the present invention to provide an intraocular pressure measuring apparatus which will save a wasteful charging time of the condenser and shorten an intraocular pressure measurement time, and thus reduce a burden to the examiner or the examinee, in such a way that charging time of the condenser adapted to activate a driving unit for driving an air supply unit for spraying air to the cornea of the eye to be examined to execute non-contact intraocular pressure measurement to the eye will be properly set according to the current supply time to the driving unit and the intraocular pressure value obtained by the intraocular pressure measurement.

To solve the above problems, the intraocular pressure measuring apparatus of the present invention is characterized in that an intraocular pressure measuring apparatus comprises spraying means for spraying a fluid to a cornea of an eye to be examined, pressure calculating means for calculating a pressure of the fluid in the spraying means, cornea transfiguration detecting means for detecting a transfiguration state of the cornea by the fluid sprayed from the spraying means, intraocular pressure value calculating means for calculating an intraocular pressure value of the eye to be examined in accordance with results of the pressure calculating means and the cornea transfiguration detecting means, disabling means for disabling the spraying means for a desired time, and control means for changing an operating time of the disabling means.

In the above intraocular pressure measuring apparatus, the present invention is characterized in that the control means changes the operating time of the disabling means in accordance with a current supply time to the spraying means.

Also, in the above intraocular pressure measuring apparatus, the present invention is characterized in that the apparatus further comprises alignment means for automatically aligning a main body of the intraocular pressure measuring apparatus with the eye to be examined, and wherein the control means controls the alignment means according to operation of the spraying means.

Also, in the above intraocular pressure measuring apparatus, the present invention is characterized in that the apparatus further comprises switch means for switching a spraying pressure of the fluid to the cornea, and wherein the control means controls an operating time of the disabling means in accordance with the spraying pressure of the fluid switched by the switch means.

Also, in the above intraocular pressure measuring apparatus of the present invention is characterized in that the control means changes an operating time of the disabling means in accordance with the intraocular pressure value calculated by the intraocular pressure value calculating means.

DETAILED DESCRIPTION OF THE PREFERRED EMBODIMENTS

The intraocular pressure measuring apparatus of the present invention will be described by using the drawings.

(Embodiment 1)

Figure 1:
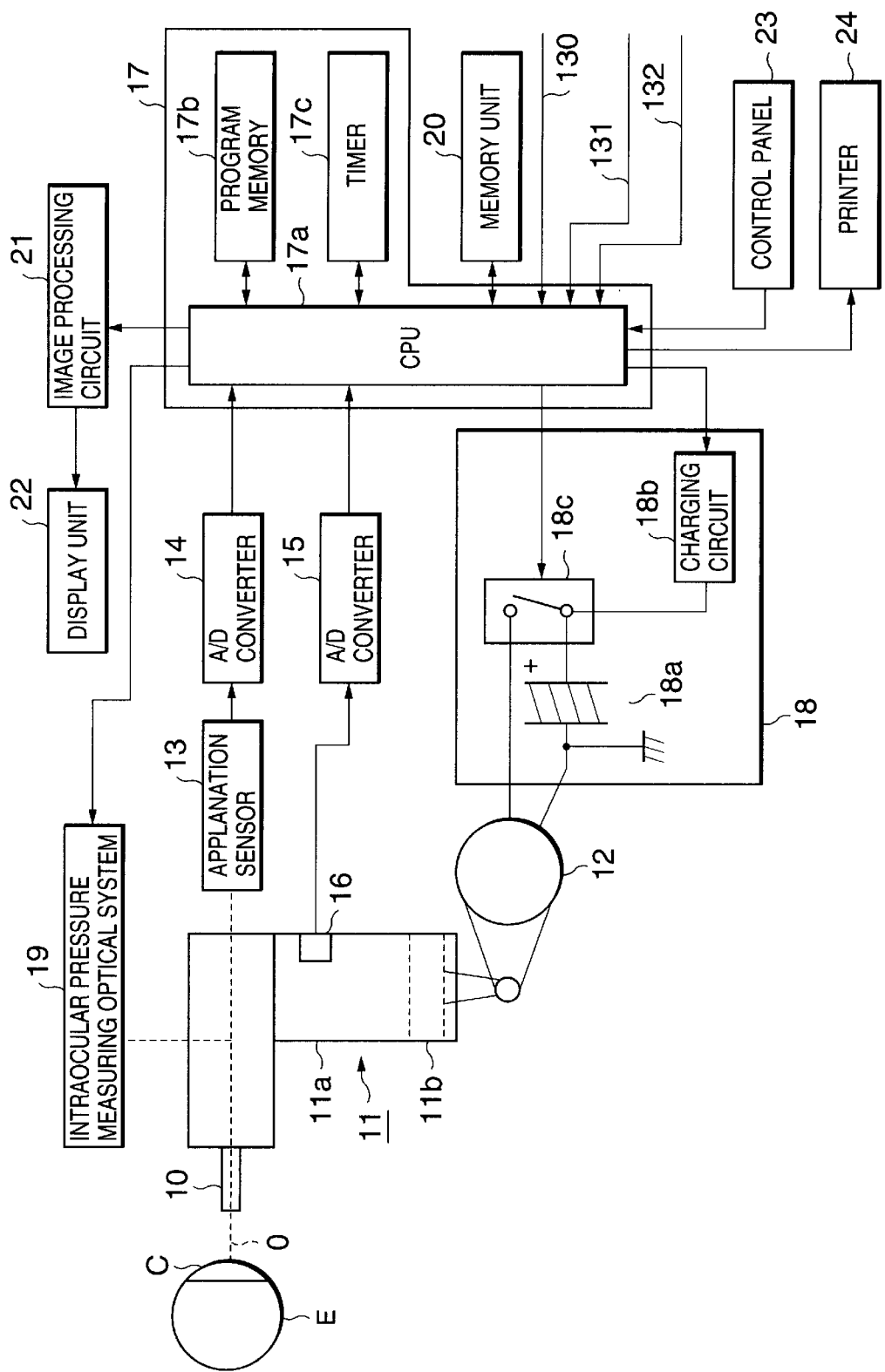
FIG. 1 is a view of the structure of the intraocular pressure measuring apparatus in accordance with a first embodiment of the present invention.

FIG. 1 shows a view of the structure of an intraocular pressure measuring apparatus according to the first embodiment of the present invention. As shown in FIG. 1, the intraocular pressure measuring apparatus has a spraying nozzle 10, an air supply unit 11, a rotary solenoid 12, an applanation sensor 13, A/D (analogue/digital) converters 14 and 15, a pressure sensor 16, a control circuit 17, a current supply unit 18, an intraocular pressure measuring optical system 19, a memory unit 20, an image processing circuit 21, a display unit 22, a control panel 23, and a printer apparatus 24.

The air supply unit 11 is constructed by a cylinder 11a and a piston 11b. The piston 11b activated by the rotary solenoid 12 compresses air within the cylinder 11a to spray air to the cornea C of the eye E to be examined of an examinee through the spraying nozzle 10.

The intraocular pressure measuring optical system 19 irradiates intraocular pressure measuring light to the cornea C of the eye E to be examined to measure intraocular pressure of the examinee at the same time when air is sprayed from the air supply unit 11 toward the cornea C.

The applanation sensor 13 electrically detects, as an applanation signal, the reflected light from the cornea C that is transfigured and flattened by air sprayed to the cornea C of the eye E to be examined through the spraying nozzle 10. The applanation signal detected by the applanation sensor 13 is converted into digital signals by the A/D converter 14, and the digital signals are output to the control circuit 17.

The pressure sensor 16 is provided in the cylinder 11a of the air supply unit 11 and electrically detects the air pressure in the cylinder 11a as a pressure signal. The pressure signal detected by the pressure sensor 16 is converted into digital signals by the A/D converter 15, and the digital signals are output to the control circuit 17.

The control circuit 17 is constructed by a CPU (Central Processing Unit) 17a, a program memory 17b, and a timer 17c. The CPU 17a controls the whole of the intraocular pressure measuring apparatus according to various control/processing programs stored in the program memory 17b. The CPU 17a also calculates values of intraocular pressure of the eye E to be examined based on applanation signals detected by the applanation sensor 13 and pressure signals detected by the pressure sensor 16. The timer 17c is used to measure current supply time to the rotary solenoid 12 at the time of non-contact intraocular pressure measurement for an examinee.

The current supply unit 18 is constructed by a condenser 18a, a charging circuit 18b; and a switch 18c. The condenser 18a is charged by the charging circuit 18b, and starts to discharge when the switch 18c is turned on by control of the CPU 17a. Accordingly, the rotary solenoid 12 is activated with current supplied from the condenser 18a.

The memory unit 20 stores data representing current supply time to the rotary solenoid 12 at the time of intraocular pressure measurement for an examinee.

The front portion image of the eye E to be examined obtained by the alignment optical system (as described later) is image-processed by the image processing circuit 21 and displayed on the display unit 22.

The control panel 23 has a two-stage switch for switching the range of intraocular pressure (0 to 30 mmHg for low intraocular pressure and 0 to 60 mmHg for high intraocular pressure), a print switch for printing the results of intraocular pressure measurement by the printer 24. At the time of intraocular pressure measurement for an examinee, an examiner pushes the two-stage switch to set the range of the intraocular pressure measurement.

Figure 2:
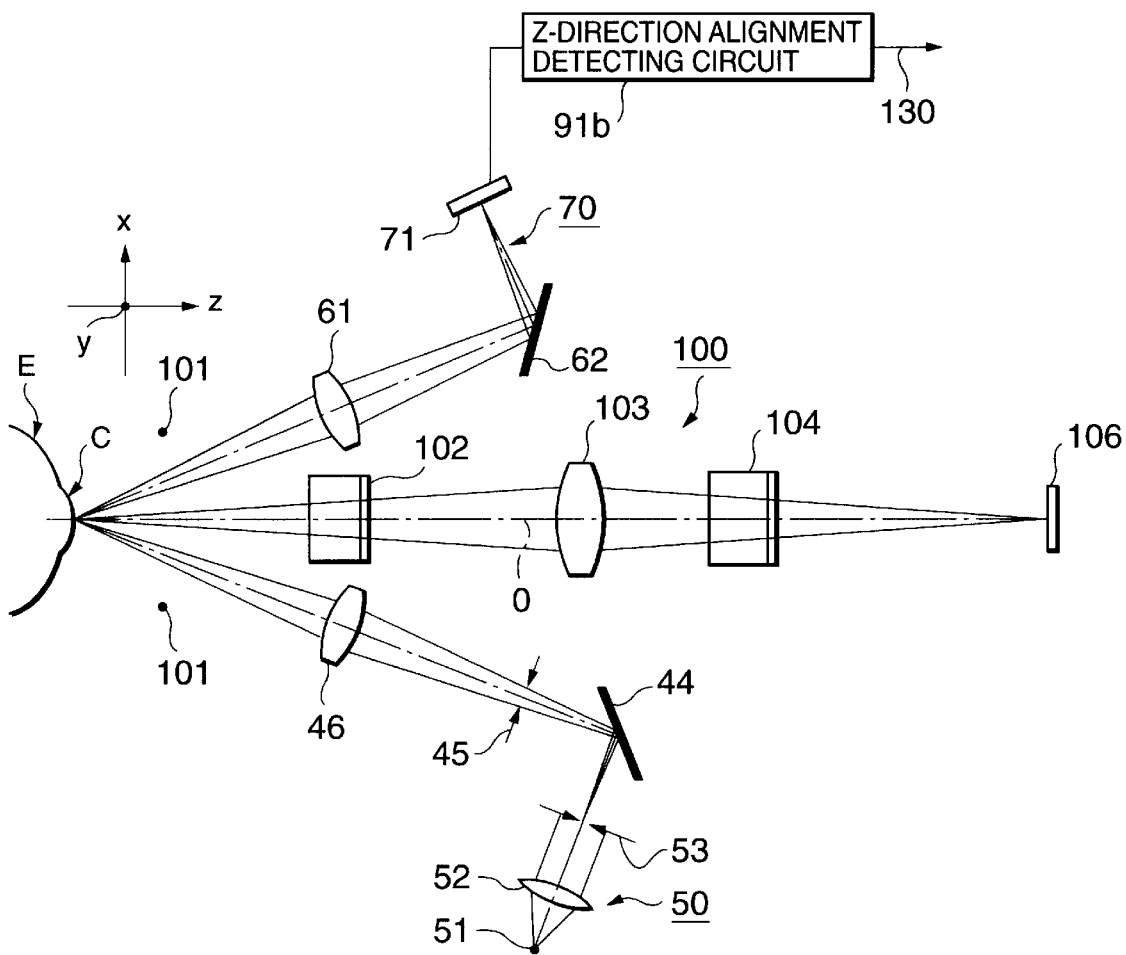
FIG. 2 is a view of the structure of the alignment optical system and the like for the intraocular pressure measuring apparatus in accordance with the first embodiment of the present invention.
Figure 3:
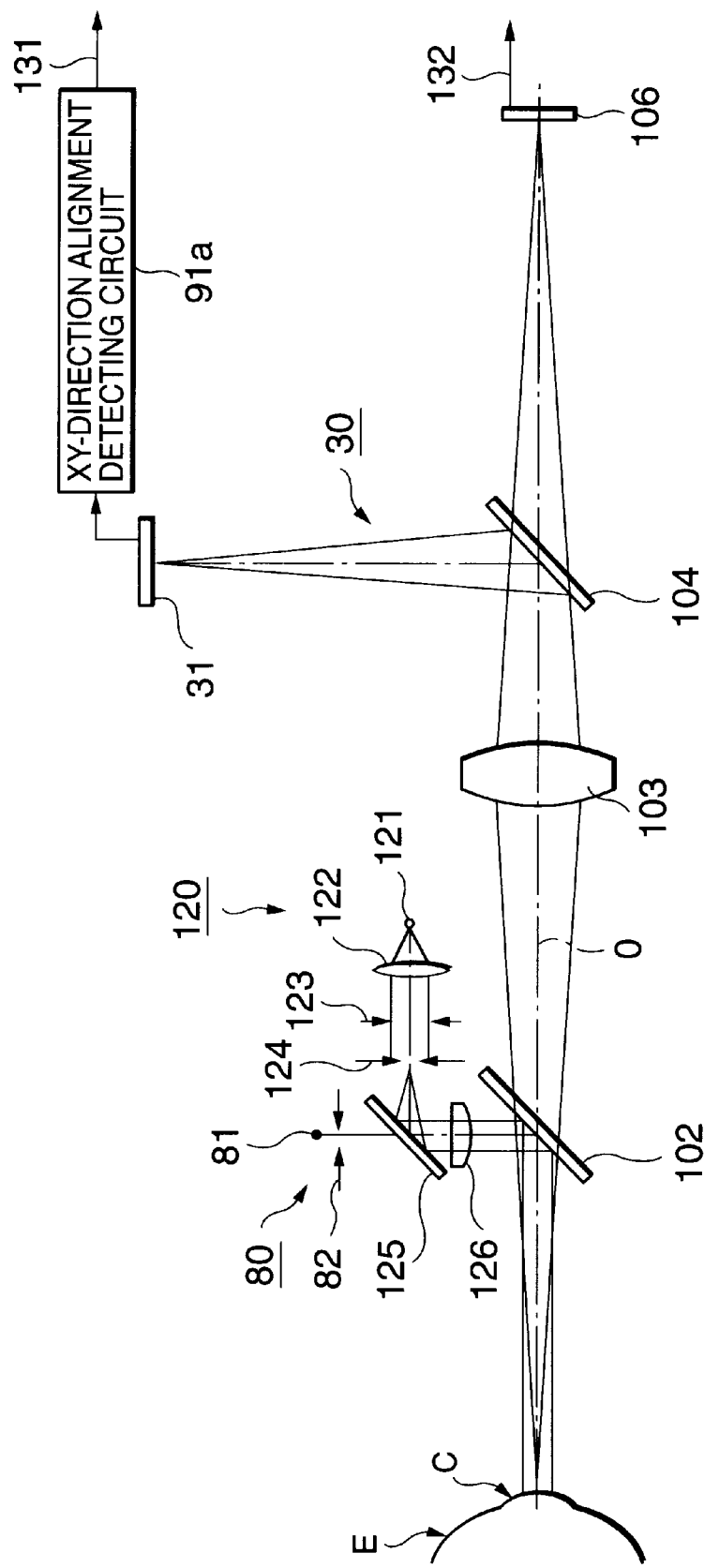
FIG. 3 is a view of the structure of the alignment optical system and the like for the intraocular pressure measuring apparatus in accordance with the first embodiment of the present invention.

FIGS. 2 and 3 show views of structures of the alignment optical system for the intraocular pressure measuring apparatus according to the first embodiment of the present invention. As shown in FIGS. 2 and 3, the intraocular pressure measuring apparatus has a front portion observing optical system 100, a target projecting optical system 120, an XY-direction alignment detecting optical system 30, a Z-direction alignment illuminating optical system 50, a Z-direction alignment detecting optical system 70, and a fixation mark projecting optical system 80. The X-direction and Y-directions represent an up-and-down direction and a right-and left direction to the face of an examinee, respectively. The Z-direction represents a vertical direction (forward and backward directions) to the face of the examinee.

The front portion observing optical system 100 for observing the front portion of the eye E to be examined has a plurality of light sources 101 provided on the rightward and leftward sides of the eye E to be examined, for illuminating the front portion of the eye E to be examined directly by infrared lights, half mirrors 102 and 104, an objective lens 103, and a CCD (charge coupled device) camera 106. The half mirrors 102 and 104, the objective lens 103 and the CCD camera 106 are arranged with an optical axis O. The front portion of the eye E to be examined is illuminated from the light sources 101. The reflected light from the front portion passes through the half mirror 102, the objective lens 103 and the half mirror 104, and is led to the CCD camera 106, so that the front portion image is obtained.

In the target projecting optical system 120, the alignment target light is projected on the cornea C of the eye E to be examined to align the main body of the intraocular pressure measuring apparatus with the eye E to be examined in XY-directions. The target projecting optical system 120 has a light source 121 for emitting infrared lights, a condenser lens 122, an aperture stop 123, a pinhole plate 124 for forming an alignment target, a dichroic mirror 125, a projection lens 126 disposed on an optical path to focus the light on the pinhole plate 124, and the half mirror 102. The infrared lights emitted from the light source 121 are converged by the condenser lens 122, passes the aperture stop 123 and is led to the pinhole plate 124. The light passed through the pinhole plate 124 is reflected by the dichroic mirror 125. At the projection lens 126 the light is rectified into parallel light flux and reflected by the half mirror 102, and then it is projected on the cornea C.

In the XY-direction alignment detecting optical system 30, the alignment target light reflected from the cornea C of the eye E to be examined is received at an alignment detecting sensor 31 to detect the relative position in XY-directions between the apparatus main body and the eye E to be examined. The XY-direction detecting optical system 30 has the half mirrors 102 and 104, the objective lens 103, and the alignment detecting sensor 31. In the target projecting optical sys em 120, the alignment target light which is projected on and reflected from the cornea C transmits the half mirror 102 and is converged by the objective lens 103. The portion of light is reflected by the half mirror 104 and made incident on the alignment detecting sensor 31. The alignment detecting sensor 31 is constructed by a light receiving element such as a PSD (Position Sensitive Device) that can detect the position of the incident light. For example, a two-dimensional PSD is used. Two units of one-dimensional PSD can be used in combination.

The XY-direction alignment detecting circuit 91a calculates the relative position in XY-directions between the apparatus main body and the eye E to be examined based on an output of the alignment detecting sensor 31 and outputs position information 131 to the control circuit 17. On the other hand, the light passing through the half mirror 104 is led to the CCD camera 106. Output information 132 of the CCD camera 106 is output to the control circuit 17, and the desired image processing is performed by the image processing circuit 21. By this image processing, the front portion image of the eye E to be examined and the alignment light spot image are displayed on the display unit 22. An examiner moves the apparatus main body in up-and-down and right-and-left directions (XY-directions) to position the alignment light spot image representing the position of the optical axis O of the apparatus optical system in an alignment area, so that the optical axis O of the apparatus optical system is aligned with the optical axis of the eyeball of the eye E to be examined.

In the Z-direction alignment illuminating optical system 50, a parallel light is irradiated from an oblique direction to the cornea C of the eye E to be examined to align the apparatus main body of the intraocular pressure measuring apparatus with the eye E to be examined in a Z-direction. The Z-directional alignment illuminating optical system 50 has a light source 51 for emitting infrared light, a condenser lens 52, a slit plate 53, a dichroic mirror 44, an aperture stop 45 and an objective lens 46. Infrared light emitted from the light source 51 is converged by the condenser lens 52, and passes the slit plate 53. The transmitted light is reflected by the dichroic mirror 44, and passes the aperture stop 45 and the objective lens 46. Then the transmitted light is irradiated on the cornea C of the eye E to be examined.

In the Z-direction alignment detecting optical system 70, slit light illuminated from the illuminating optical system 50 is reflected by the cornea C. The reflected light is received at an alignment detecting sensor 71 to detect a Z-directional position. The Z-direction alignment detecting optical system 70 has an objective lens 61, a dichroic mirror 62, and the alignment detecting sensor 71. The slit light reflected by the cornea C is converged by the objective lens 61, and then is led to the dichroic mirror 62. Further, the light is reflected by dichroic mirror 62 and made incident upon the alignment detecting sensor 71. The alignment detecting sensor 71 is constructed by a light receiving element such as a line sensor (PSD) with which a distribution of the quantity of light can be detected.

A Z-direction alignment detecting circuit 91b detects the peak position of the quantity of light based on the output of the alignment detecting sensor 71, so that the relative position in a Z-direction is detected. The position information 130 is output from the Z-directional alignment detecting circuit 91b to the control circuit 17. The information representing a working distance calculated based on this position information is displayed on the display unit 22 through the image processing circuit 21.

The examiner moves the apparatus main body in the backward and forward direction (Z-direction) to the eye E to be examined by reference to the information representing the working distance so as to secure the desired working distance. The working distance is a distance between the top of the cornea C of the eye E to be examined and the tip of the spraying nozzle 10, which is set by the examiner and stored in the memory unit 20.

The fixation mark projecting optical system 80 for projecting a fixation mark image on the eye E to be examined has a light source 81 for emitting visible light, a pinhole plate 82, the dichroic mirror 125, the projection lens 126, and the half mirror 102. visible light emitted from the light source 81 is reflected by the dichroic mirror 125, passes the pinhole plate 82, and is rectified into parallel light flux by projection lens 126. The parallel light flux is reflected by the half mirror 102 and is projected on the eye E to be examined. The line of sight of the eye E to be examined is fixed by closely observing the fixation mark light as a fixation target.

The operation of intraocular pressure measuring apparatus according to the first embodiment of the present invention will be described below.

Figure 4:
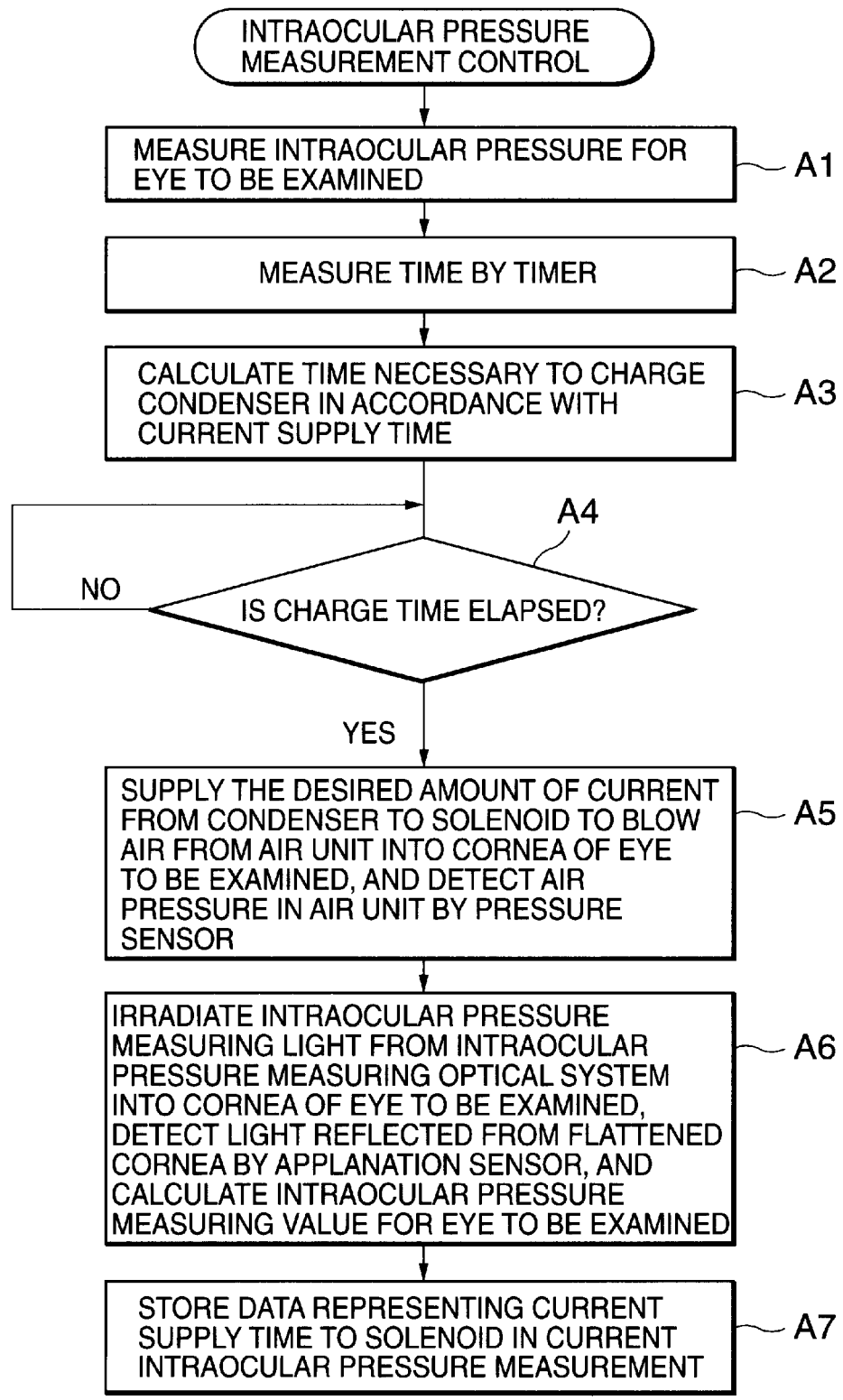
FIG. 4 is a view of an intraocular pressure measurement control flow chart for the intraocular pressure measuring apparatus in accordance with the first embodiment of the present invention.

FIG. 4 is an intraocular pressure measurement control flow chart of the intraocular pressure measuring apparatus according to the first embodiment of the present invention. In step A1, after alignment is completed, the first intraocular pressure measurement is performed by the above known method. In this time, the timer 17c measures a current supply time to the rotary solenoid 12 (step A2).

In step A3, time required for fully charging the condenser 18a is calculated in accordance with the current supply time measured by the timer 17c.

The following description deals with relations of the current supply time and the time required for charging.

Figure 5:
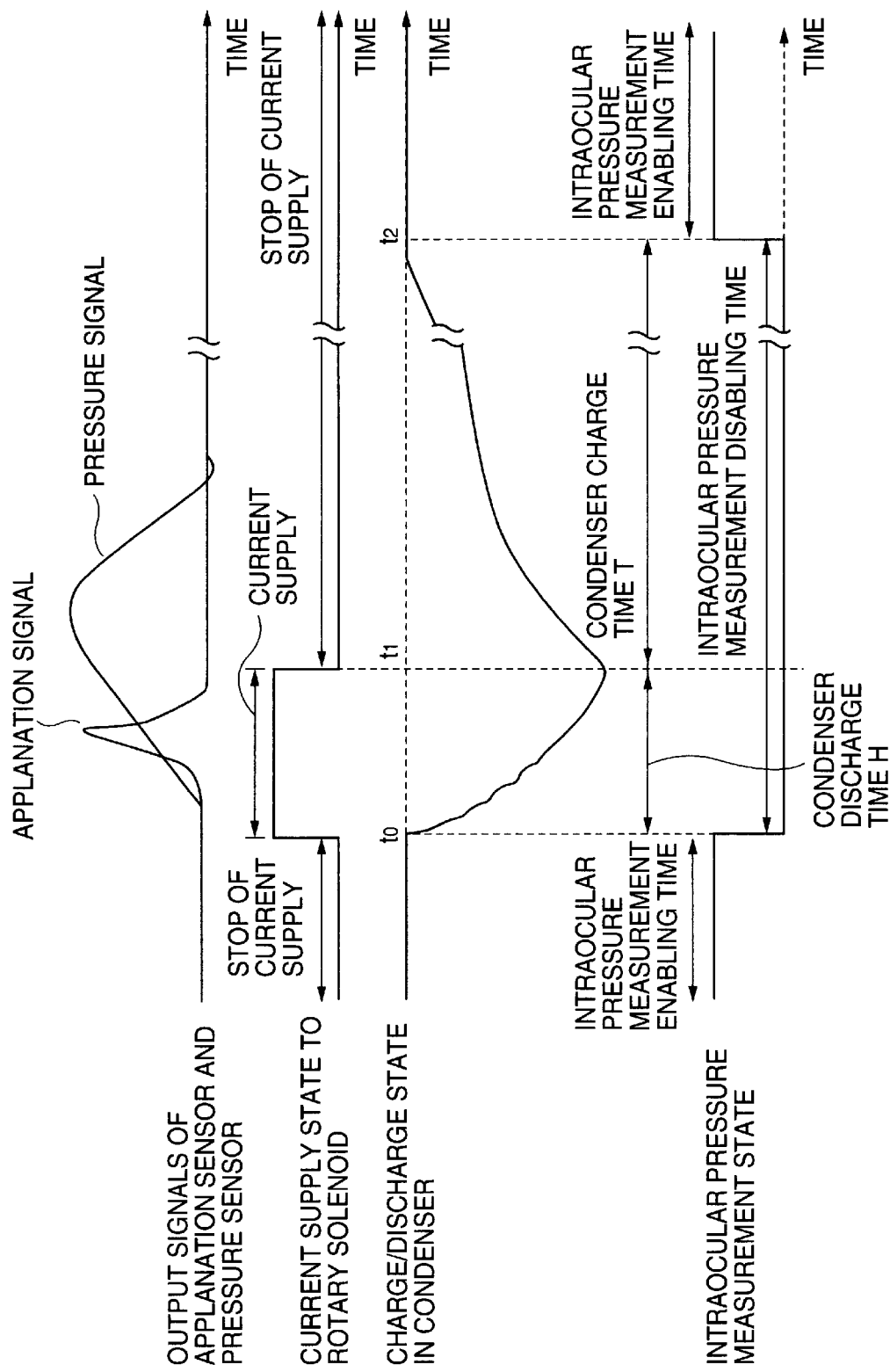
FIG. 5 shows a pressure signal representing output of a pressure sensor, applanation signal representing output of an applanation sensor, current supply/stop to a rotary solenoid, charging/discharging time of the condenser, intraocular pressure measurement enabling time and intraocular pressure measurement disabling time in the intraocular pressure measuring apparatus in accordance with the first embodiment of the present invention.

FIG. 5 is a diagram of a pressure signal representing output of the pressure sensor 16, an applanation signal representing output of the applanation sensor 13, current supply/stop to the rotary solenoid 12, charging/discharging time of the condenser 18a, intraocular pressure enabling time, and intraocular pressure disabling time in the intraocular pressure measuring apparatus according to the first embodiment of the present invention. In FIG. 5, the pressure signal represents the output signal of the pressure sensor 16 that detects air pressure in the cylinder 11a as an electric signal when air is sprayed from the spraying nozzle 10 to the cornea C of the eye E to be examined, while the applanation signal represents the output signal of the applanation sensor 13 that detects as an electric signal, the intraocular pressure measuring light reflected from the cornea C at the same time when the cornea C is transfigured and flattened by air sprayed from the spraying nozzle 10.

The applanation signal, the output signal of the applanation sensor 13, and the pressure signal, the output signal of the pressure sensor 16 are respectively converted into digital signals by the A/D converters 14 and 15, and then output to the CPU 17a of the control circuit 17. The CPU 17a calculates the intraocular pressure value based on the applanation signal and the pressure signal using the desired formula.

After confirming the applanation signal, the CPU 17a turns off the switch 18c to stop the current supply to the solenoid 12. Therefore, the operation of the solenoid 12 is stopped, and the air spraying operation of the air supply unit 11 is stopped, so that air pressure in the piston 11b is lowered.

The higher the intraocular pressure of the eye E to be examined is, later the applanation signal appears after air spray. That is, if the intraocular pressure of the eye E to be examined is higher, since more air must be sprayed from the air supply unit 11 to flatten the cornea C of the eye E to be examined, it will take longer time to supply more current to the solenoid 12. Thus, since the discharging time H of the condenser 18a as energy source becomes longer, the charging time T of the condenser 18a also becomes longer.

The CPU 17a determines the discharging level of the condenser 18a by confirming the current supply time to the solenoid 12. Based on the determination result, the time required for charging the condenser 18a can be calculated.

In step A4, it is determined whether or not the time required for charging the condenser 18a elapses as calculated in step A3 after the discharging of the condenser 18a.

Since the charging time is measured by the timer 17c, the read-out charging time is compared with the required charging time calculated in step A3. Thus, it can be determined whether or not it is possible to start the next intraocular pressure measurement. If the sufficient time does not elapse, the intraocular pressure measurement is not started.

On the other hand, when the time required for charging the condenser 18a elapses as calculated in step A4, since the condenser 18a is fully charged, it is possible to execute intraocular pressure measurement. Accordingly, in step A5, the switch 18c is turned on. Therefore, the desired quantity of current is supplied from the condenser 18a to the solenoid 12 to activate the solenoid 12. By the activated solenoid 12, the piston 11b of the air supply unit 11 is operated to compress air in the cylinder 11a and spray the compressed air to the cornea C of the eye E to be examined through the spraying nozzle 10. Further, air pressure in the cylinder 11a (chronological pressure change) is detected as a pressure signal by the pressure sensor 16. Thus, in the first embodiment of the present invention, since the time required for charging the condenser 18a is calculated, it is possible to eliminate a wasteful waiting time in intraocular pressure measurement.

In step A6, the intraocular pressure measuring light is irradiated toward the cornea C of the eye E to be examined from the intraocular pressure measuring optical system 19. Thus, the light reflected from the cornea C that is transfigured and flattened by the sprayed air is detected as an applanation signal by the applanation sensor 13. The intraocular pressure value of the eye E to be examined is calculated using the desired formula in accordance with the pressure signal detected by the pressure sensor 16 and the applanation signal detected by the applanation sensor 13.

In step A7, the current supply time to the solenoid 12 at the time of current intraocular pressure measurement (second intraocular pressure measurement) is measured by the timer 17c. The data representing the measured current supply time is stored in the memory unit 20. The data is used for the third intraocular pressure measurement that is performed next. By the control operation as described above, when the three intraocular pressure measurements are completed, the average value of the three measurement values are printed by the printer 24.

In the case of an intraocular pressure measuring apparatus with a automatic alignment adjusting function, the automatic alignment adjustment is not performed during the intraocular pressure measurement disabling period. This is because it is not possible to measure intraocular pressure if the automatic alignment adjustment is performed. Accordingly, in the intraocular pressure measuring apparatus with the automatic alignment adjustment function, during a charging period of the condenser 18a, the automatic alignment adjustment is not disabled to avoid wasteful operation to the apparatus. Therefore, it is possible to save power consumption in the intraocular pressure measuring apparatus, thereby to shorten intraocular pressure measurement time.

However, the intraocular pressure measuring apparatus can be designed in such a manner that before the completion of charging of the condenser 18a the automatic alignment adjustment starts, and completes immediately before or immediately after the completion of charging of the condenser 18a. For example, assuming that the charging completion time t2 of the condenser 18a is calculated based on the time required for charging the condenser 18a as calculated in step A3. Then, considering the average time Tave required for the automatic alignment adjust ent, an automatic alignment driving unit (not shown) is unlock d-at time (t2 minus Tave), Tave earlier than time t2, to start automatic alignment adjustment. Thus, it is possible to further shorten the intraocular pressure measurement time.

(Embodiment 2)

In the intraocular pressure measuring apparatus according to a second embodiment of the present invention, the discharging quantity of the condenser 18a is determined according to the measured intraocular pressure value of the eye E to be examined. Based on the determination result, the time required for charging the condenser 18a is calculated. The higher the intraocular pressure value of the eye E to be examined is, the more the spraying air to the cornea C is required. It is necessary to extend the current supply time to the solenoid 12 accordingly.

It is possible to use a table stored in advance in the memory unit 20 instead of making calculation to determine the discharging quantity of the condenser 18a. The table has data wherein the intraocular pressure value of the eye E to be examined and the discharging quantity (current quantity) of the condenser 18a are in pairs.

(Embodiment 3)

In the intraocular pressure measuring apparatus according to a third embodiment of the present invention, the discharging quantity of the condenser 18a is determined by detecting the maximum value of the pressure signal by the pressure sensor 16 without calculating the intraocular pressure value of the eye E to be examined. Based on the determination result, the charging time required for the condenser 18a is calculated.

The discharging quantity of the condenser 18a may be determined by using the table stored in advance in the memory unit 20 instead of making the calculation. The table has for example, data wherein the maximum value of the pressure signal and the discharging quantity (current quantity) of the condenser 18a are in pairs.

(Embodiment 4)

In the intraocular pressure measuring apparatus with a switching function for the measurement range of high intraocular pressure and low intraocular pressure, according to a fourth embodiment of the present invention, the intraocular pressure measurement disabling time is set in a two-stage according to the intraocular pressure measurement range to the examinee. Thus, it is possible to reduce the load to the CPU 17a and shorten the processing time of the CPU 17a.

(Embodiment 5)

The intraocular pressure measuring apparatus according to a fifth embodiment of the present invention has both of function as noted in the above embodiment and charging voltage detection function for the condenser 18a. Thus, it is possible to grasp the intraocular pressure measurement disabling time securely and to deal with possible degradation of the condenser 18a. In this case, the method for detecting a charging voltage of the condenser 18a can be simplified.

Whether or not the condenser 18a is completely charged is determined by detecting the charging voltage of the condenser 18a using an electric circuit (not shown) such as an operational amplifier and a comparator.

As described above, according to the present invention, it is possible to adequately set an intraocular pressure measurement disabling time suitable to charge the condenser used as energy source for spraying air in intraocular pressure measurement, so that a wasteful intraocular pressure measurement can be avoided and intraocular pressure measurement time can be shortened. Thus, it is possible to considerably reduce the burden to the examiner and the examinee.

What is claimed is:

1. An intraocular pressure measuring apparatus comprising:

spraying means for spraying a fluid to a cornea of an eye to be examined;

pressure calculating means for calculating a pressure of the fluid in the spraying means;

cornea transfiguration detecting means for detecting a transfiguration state of the cornea by the fluid sprayed from the spraying means;

intraocular pressure value calculating means for calculating an intraocular pressure value of the eye to be examined in accordance with results of the pressure calculating means and the cornea transfiguration detecting means;

disabling means for disabling the spraying means for a desired time; and control means for changing an operating time of the disabling means.

2. The intraocular pressure measuring apparatus according to claim 1, wherein the control means changes the operating time of the disabling means in accordance with a current supply time to the spraying means.

3. The intraocular pressure measuring apparatus according to claim 1, further comprising alignment means for automatically aligning a main body of the intraocular pressure measuring apparatus with the eye to be examined, and wherein the control means controls the alignment means according to operation of the spraying means.

4. The intraocular pressure measuring apparatus according to claim 1, further comprising switch means for switching a spraying pressure of the fluid to the cornea, and wherein the control means controls an operating time of the disabling means in accordance with the spraying pressure of the fluid switched by the switch means.

5. The intraocular pressure measuring apparatus according to claim 4, further comprising alignment means for automatically aligning a main body of the intraocular pressure measuring apparatus with the eye to be examined, and wherein the control means controls the alignment means in accordance with operation of the spraying means.

6. The intraocular pressure measuring apparatus according to claim 1, wherein the control means changes an operating time of the disabling means in accordance with the intraocular pressure value calculated by the intraocular pressure value calculating means.

* * * * *